United States Patent
Fischer et al.

(10) Patent No.: US 7,312,356 B2
(45) Date of Patent: Dec. 25, 2007

(54) MEDICAMENT

(75) Inventors: Peter Martin Fischer, Angus (GB); Jan Sarek, Ostrava-Poruba (CZ); Paul M. Blaney, Burnley (GB); Piers Collier, Didsbury (GB); John R. Ferguson, Radcliffe (GB); Jonathan D. Hull, High Peak (GB)

(73) Assignee: Cyclacel Limited, Dundee (GB)

(*) Notice: Subject to any disclaimer, the term of this patent is extended or adjusted under 35 U.S.C. 154(b) by 237 days.

(21) Appl. No.: 10/846,217

(22) Filed: May 14, 2004

(65) Prior Publication Data

US 2005/0159484 A1  Jul. 21, 2005

Related U.S. Application Data

(63) Continuation of application No. PCT/GB02/05231, filed on Nov. 21, 2002.

(30) Foreign Application Priority Data

Nov. 22, 2001 (GB) ................................ 0128071.8

(51) Int. Cl.
*C07C 67/02* (2006.01)
*A61K 31/225* (2006.01)

(52) U.S. Cl. ........................................ 560/257; 514/548

(58) Field of Classification Search ...................... None
See application file for complete search history.

(56) References Cited

U.S. PATENT DOCUMENTS 5,468,888 A * 11/1995 Bouboutou et al. ........... 554/58
5,679,644 A * 10/1997 Rao et al. ..................... 514/26
5,885,992 A *  3/1999 Ohgi et al. .................. 514/245

FOREIGN PATENT DOCUMENTS

WO    WO 01/90136 A2    11/2001
WO    WO 01/90136 A3    11/2001

OTHER PUBLICATIONS

Eckerman, et al. Paperi Ja Puu. 1985. 67(3):100-106.
Fujioka, et al., Antitumor Agents 171. Cytotoxicities of Lobatosides B,C,D, and E, Cyclic Bisdesmosides Isolated from Actinostemma Lobatum Maxim. Biorganic & Medicinal Chemistry Letters. 1996. 6(23):2807-2810.
Sarek, et al. Stepeni Dvojne Vazy v Derivatech 18-Lupenu Oxidem Ruthenicelym-Cesta K Des-E-Lupanovym Slouceninam. Journal of Chemistry. 1997. 91:1005-1006.
Sejbal, et al. Oxidation of 3β,28-Lupanediol Diacetate and Lupane with Peroxyacetic Acid. Collect. Czech Chem. Commun. 1987. 52:487-492.
Soukas, et al., Triterpenes. A Novel Acid Catalysed Double Bond Migration in 3β, 28-Diacetoxy-lup-20(30)-ene (Betulin Diacetate). Acta Chem. Scand. 1975. B29(1):139-40.

* cited by examiner

*Primary Examiner*—Sikarl A. Witherspoon
(74) *Attorney, Agent, or Firm*—Lahive & Cockfield, LLP; Cynthia L. Kanick; Cynthia M. Soroos, Esq.

(57) ABSTRACT

The present invention relates to 3β,28-diacetoxy-18-oxo-19,20,21,29,30-pentanorlupan-22-oic acid methanol solvate, its use in medicine and processes for its preparation.

15 Claims, 2 Drawing Sheets

MEDICAMENT

RELATED APPLICATIONS

This application is a continuation of PCT/GB02/05231, filed on Nov. 21, 2002, which claims priority to GB 0128071.8, filed on Nov. 22, 2001, the entire contents of each of which are hereby incorporated herein by reference.

FIELD OF THE INVENTION

The present invention relates to 3β,28-diacetoxy-18-oxo-19,20,21,29,30-pentanorlupan-22-oic acid methanol solvate, its use in medicine and processes for its preparation.

BACKGROUND OF THE INVENTION

The compound 3β,28-diacetoxy-18-oxo-19,20,21,29,30-pentanorlupan-22-oic acid was first described in Chem. Listy 91, 1005 (1997), Šarek J. et al. Its molecular formula may be represented as:

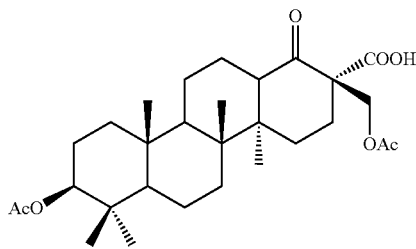

This compound has recently shown promise in the treatment of proliferative disorders such as cancers and leukaemias.

Accordingly there is a need for improved forms of this compound having improved properties as well as new processes for its manufacture and the manufacture of its process intermediates.

SUMMARY OF THE INVENTION

We have now surprisingly found that crystals of 3β,28-diacetoxy-18-oxo-19,20,21,29,30-pentanorlupan-22-oic acid grown from a $CHCl_3$/EtOAc/MeOH solvent system affords a new and improved form of 3β,28-diacetoxy-18oxo-19,20,21,29,30-pentanorlupan-22-oic acid identified as 3β,28-diacetoxy-18-oxo-19,20,21,29,30-pentanorlupan-22-oic acid methanol solvate.

Thus, in a first aspect the present invention provides 3β,28-diacetoxy-18-oxo-19,20,21,29,30-pentanorlupan-22-oic acid methanol solvate. In particular, the present invention provides 3β,28-diacetoxy-18-oxo-19,20,21,29,30-pentanorlupan-22-oic acid•1.5MeOH.

3β,28-diacetoxy-18-oxo-19,20,21,29,30-pentanorlupan-22-oic acid•1.5MeOH may possess one or more of the following advantages as compared to the non-solvated precursor: improved aqueous solubility, uniform size distribution, filtration and drying characteristics, stability (thermal or long term storage), flowability, handling characteristics, isolation and purification characteristics, and physical properties advantageous to formulatory requirements e.g. compressibility.

DETAILED DESCRIPTION OF THE INVENTION

Figure 1:
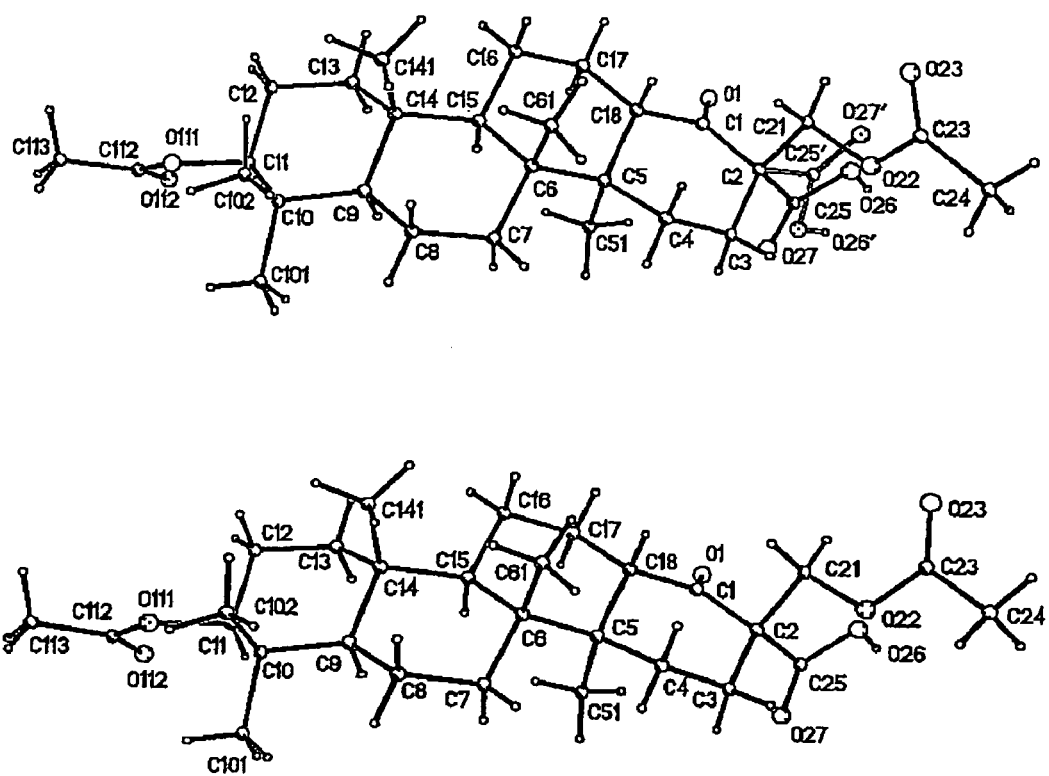
FIG. 1 illustrates the molecular structure of the two independent molecules of 3β,28-diacetoxy-18-oxo-19,20, 21,29,30-pentanorlupan-22-oic acid•1.5MeOH present in the unit cell.

Thus in a further aspect the present invention provides 3β,28-diacetoxy-18-oxo-19,20,21,29,30-pentanorlupan-22-oic acid methanol solvate having at least X-ray diffraction peaks at 14.7 and 16.0. Preferably the powder X-ray diffraction pattern will have peaks at 14.7, 16.0, 16.7, 18.8, 8.3, 20.4, 22.7. More preferably, the powder X-ray diffraction pattern will have peaks at 14.7, 16.0, 16.7, 14.4, 18.8, 8.3, 20.4, 15.7, 22.7. Most preferably, the X-ray diffraction pattern will be substantially as described in FIG. 2.

The unit cell dimension for 3β,28-diacetoxy-18-oxo-19, 20,21,29,30-pentanorlupan-22-oic acid•1.5MeOH were determined as described in the examples.

Thus in a further aspect the present invention provides 3β,28-diacetoxy-18-oxo-19,20,21,29,30-pentanorlupan-22-oic acid methanol solvate having unit cell dimensions a=(7).4459(9) Å, α=90°, b=11.0454(9) Å, β=94.002(11)°, c=36.178(4) Å, γ=90°.

The atomic co-ordinates for 3β,28-diacetoxy-18-oxo-19, 20,21,29,30-pentanorlupan-22-oic acid•1.5MeOH were determined as described in the examples.

Thus in a further aspect the present invention provides 3β,28-diacetoxy-18-oxo-19,20,21,29,30-pentanorlupan-22-oic acid methanol solvate having atomic co-ordinates substantially as set down in Table 2.

Analysis of the 3β,28-diacetoxy-18-oxo-19,20,21,29,30-pentanorlupan-22-oic acid•1.5 MeOH revealed it to be a monoclinic crystalline form.

Thus, in a further aspect the present invention provides crystalline 3β,28-diacetoxy-18-oxo-19,20,21,29,30-pentanorlupan-22-oic acid methanol solvate wherein the crystalline form is monoclinic.

3β,28-diacetoxy-18-oxo-19,20,21,29,30-pentanorlupan-22-oic acid methanol solvate may be presented as salts or esters, in particular pharmaceutically acceptable salts or esters.

Pharmaceutically acceptable salts of 3β,28-diacetoxy-18-oxo-19,20,21,29,30-pentanorlupan-22-oic acid methanol solvate include suitable acid addition or base salts thereof. A review of suitable pharmaceutical salts may be found in Berge et al, J Pharm Sci, 66, 1-19 (1977). Suitable salts according to the invention include those formed with both organic and inorganic acids and bases. Pharmaceutically acceptable acid addition salts include those formed from hydrochloric, hydrobromic, sulphuric, citric, tartaric, phosphoric, lactic, pyruvic, acetic, trifluoroacetic, succinic, oxalic, fumaric, maleic, oxaloacetic, methanesulphonic, ethanesulphonic, p-toluenesulphonic, benzenesulphonic and isethionic acids. Pharmaceutically acceptable base salts include ammonium salts, alkali metal salts such as those of sodium and potassium, alkaline earth metal salts such as those of calcium and magnesium and salts with organic bases such as dicyclohexyl amine and N-methyl-D-glucamine.

Esters are formed either using organic acids or alcohols/hydroxides, depending on the functional group being esterified. Organic acids include carboxylic acids, such as alkanecarboxylic acids of 1 to 12 carbon atoms which are unsubstituted or substituted (e.g., by halogen), such as acetic acid; with saturated or unsaturated dicarboxylic acid, for example oxalic, malonic, succinic, maleic, fumaric, phthalic or tetraphthalic; with hydroxycarboxylic acids, for example ascorbic, glycolic, lactic, malic, tartaric or citric acid; with aminoacids, for example aspartic or glutamic acid; with benzoic acid; or with organic sulfonic acids, such as ($C_1$-$C_4$)-alkyl- or aryl-sulfonic acids which are unsubstituted or substituted (for example, by a halogen) such as methane- or p-toluene sulfonic acid. Suitable hydroxides include inorganic hydroxides, such as sodium hydroxide, potassium hydroxide, calcium hydroxide, aluminium hydroxide. Alcohols include alkanealcohols of 1-12 carbon atoms which may be unsubstituted or substituted, e.g. by a halogen).

The invention includes all enantiomers and tautomers of 3β,28-diacetoxy-18-oxo-19,20,21,29,30-pentanorlupan-22-oic acid methanol solvate. The man skilled in the art will recognise that 3β,28-diacetoxy-18-oxo-19,20,21,29,30-pentanorlupan-22-oic acid methanol solvate possess optical properties (one or more chiral carbon atoms) and tautomeric characteristics. The corresponding enantiomers and/or tautomers may be isolated/prepared by methods known in the art.

The invention furthermore relates to 3β,28-diacetoxy-18-oxo-19,20,21,29,30-pentanorlupan-22-oic acid methanol solvate in its various crystalline and polymorphic and (an) hydrous forms.

Thus, the present invention further provides a pharmaceutical composition comprising 3β,28-diacetoxy-18-oxo-19,20,21,29,30-pentanorlupan-22-oic acid methanol solvate or pharmaceutically acceptable salt or esters thereof, together with at least one pharmaceutically acceptable excipient, diluent or carrier.

By way of example, in the pharmaceutical compositions of the present invention, 3β,28-diacetoxy-18-oxo-19,20,21,29,30-pentanorlupan-22-oic acid methanol solvate may be admixed with any suitable binder(s), lubricant(s), suspending agent(s), coating agent(s), and/or solubilising agent(s). Examples of such suitable excipients for the various different forms of pharmaceutical compositions described herein may be found in the "Handbook of Pharmaceutical Excipients, $2^{nd}$ Edition, (1994), Edited by A Wade and P J Weller.

As mentioned previously, 3β,28-diacetoxy-18-oxo-19,20,21,29,30-pentanorlupan-22-oic acid has recently shown promise in the treatment of proliferative disorders such as cancers and leukaemias. Accordingly, in another aspect the present invention provides 3β,28-diacetoxy-18-oxo-19,20,21,29,30-pentanorlupan-22-oic acid methanol solvate for use in therapy, in particular for use in the manufacture of a medicament for the treatment of proliferative disorders such as cancers and leukaemias.

In the alternative, the present invention provides a method of treating proliferative disorders, preferably cancer and/or leukaemia, in a mammal, including a human, which comprises administering an effective amount of 3β,28-diacetoxy-18-oxo-19,20,21,29,30-pentanorlupan-22-oic acid methanol solvate to said mammal.

The present invention also encompasses pharmaceutical compositions comprising 3β,28-diacetoxy-18-oxo-19,20,21,29,30-pentanorlupan-22-oic acid methanol solvate. In this regard, and in particular for human therapy, even though 3β,28-diacetoxy-18-oxo-19,20,21,29,30-pentanorlupan-22-oic acid methanol solvate (including its pharmaceutically acceptable salts, esters and pharmaceutically acceptable solvates) may be administered alone, it will generally be administered in admixture with a pharmaceutical carrier, excipient or diluent selected with regard to the intended route of administration and standard pharmaceutical practice.

The pharmaceutical compositions of the present invention may be adapted for oral, rectal, vaginal, parenteral, intramuscular, intraperitoneal, intraarterial, intrathecal, intrabronchial, subcutaneous, intradermal, intravenous, nasal, buccal or sublingual routes of administration.

For oral administration, particular use is made of compressed tablets, pills, tablets, gellules, drops, and capsules. Preferably, these compositions contain from 1 to 250 mg and more preferably from 10-100 mg, of active ingredient per dose.

Other forms of administration comprise solutions or emulsions which may be injected intravenously, intraarterially, intrathecally, subcutaneously, intradermally, intraperitoneally or intramuscularly, and which are prepared from sterile or sterilisable solutions. The pharmaceutical compositions of the present invention may also be in form of suppositories, pessaries, suspensions, emulsions, lotions, ointments, creams, gels, sprays, solutions or dusting powders.

An alternative means of transdermal administration is by use of a skin patch. For example, the active ingredient can be incorporated into a cream consisting of an aqueous emulsion of polyethylene glycols or liquid paraffin. The active ingredient can also be incorporated, at a concentration of between 1 and 10% by weight, into an ointment consisting of a white wax or white soft paraffin base together with such stabilisers and preservatives as may be required.

Injectable forms may contain between 10-1000 mg, preferably between 10-250 mg, of active ingredient per dose.

Compositions may be formulated in unit dosage form, i.e., in the form of discrete portions containing a unit dose, or a multiple or sub-unit of a unit dose.

A person of ordinary skill in the art can easily determine an appropriate dose of one of the instant compositions to administer to a subject without undue experimentation. Typically, a physician will determine the actual dosage which will be most suitable for an individual patient and it will vary with the age, weight and response of the particular patient. The dosages disclosed herein are exemplary of the average case. There can of course be individual instances where higher or lower dosage ranges are merited, and such are within the scope of this invention.

In an exemplary embodiment, one or more doses of 10 to 150 mg/day will be administered to the patient for the treatment of an antiproliferative disorder.

In a particularly preferred embodiment, the one or more compounds of the invention are administered in combination with one or more other anticancer agents, for example, existing anticancer drugs available on the market. In such cases, the compounds of the invention may be administered consecutively, simultaneously or sequentially with the one or more other anticancer agents.

Anticancer drugs in general are more effective when used in combination. In particular, combination therapy is desirable in order to avoid an overlap of major toxicities, mechanism of action and resistance mechanism(s). Furthermore, it is also desirable to administer most drugs at their maximum tolerated doses with minimum time intervals between such doses. The major advantages of combining chemotherapeutic drugs are that it may promote additive or possible synergistic effects through biochemical interactions and also may decrease the emergence of resistance in early tumor cells which would have been otherwise responsive to initial chemotherapy with a single agent. An example of the use of biochemical interactions in selecting drug combinations is demonstrated by the administration of leucovorin to increase the binding of an active intracellular metabolite of 5-fluorouracil to its target, thymidylate synthase, thus increasing its cytotoxic effects.

Numerous combinations are used in current treatments of cancer and leukemia. A more extensive review of medical practices may be found in "Oncologic Therapies" edited by E. E. Vokes and H. M. Golomb, published by Springer.

Beneficial combinations may be suggested by studying the growth inhibitory activity of the test compounds with agents known or suspected of being valuable in the treatment of a particular cancer initially or cell lines derived from that cancer. This procedure can also be used to determine the order of administration of the agents, i.e. before, simultaneously, or after delivery. Such scheduling may be a feature of all the cycle acting agents identified herein.

3β,28-diacetoxy-18-oxo-19,20,21,29,30-pentanorlupan-22-oic acid methanol solvate may be prepared by crystallising 3β,28-diacetoxy-18-oxo-19,20,21,29,30-pentanorlupan-22-oic acid from a $CHCl_3$/EtOAc/MeOH solvent system.

Thus in a further aspect the present invention provides a process for preparing 3β,28-diacetoxy-18-oxo-19,20,21,29,30-pentanorlupan-22-oic acid methanol solvate which comprises crystallising 3β,28-diacetoxy-18-oxo-19,20,21,29,30-pentanorlupan-22-oic acid from a $CHCl_3$/EtOAc/MeOH solvent system. 3β,28-diacetoxy-18-oxo-19,20,21,29,30-pentanorlupan-22-oic acid (7) may be prepared from betulin (1) according to Scheme 1 set out below.

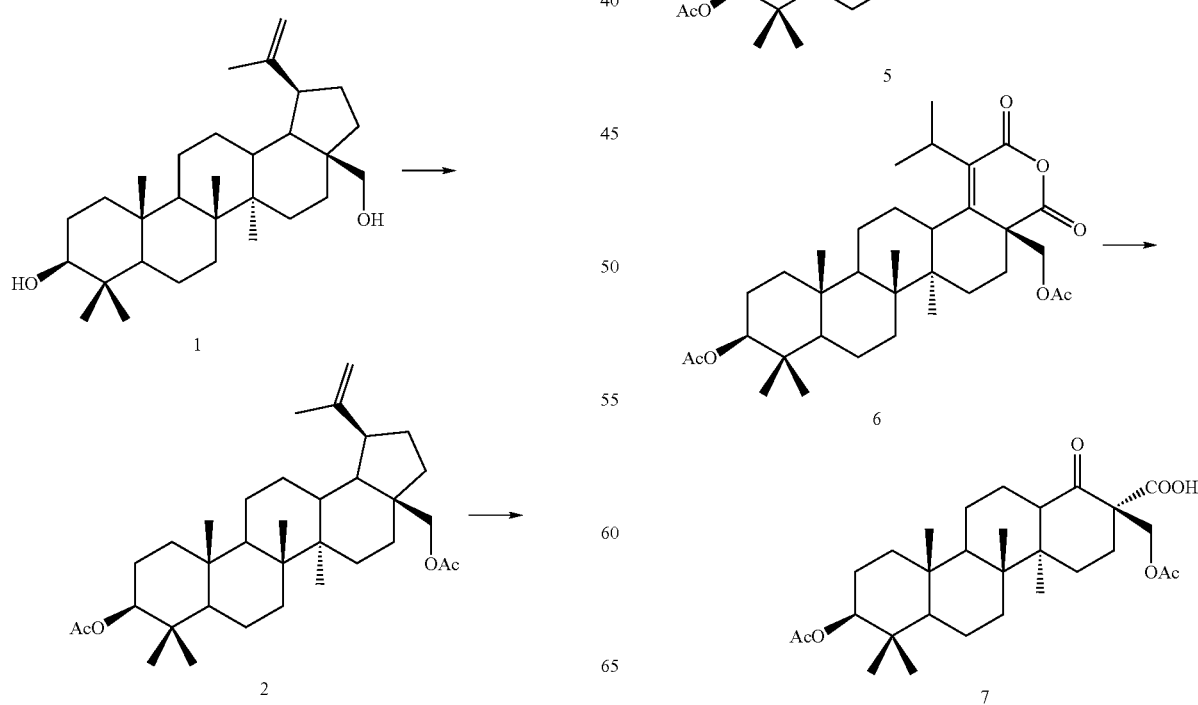

Scheme 1

Essentially the process entails oxidative degradation of the lupane cyclopentane ring is such a way as to install the requisite β-ketoacid group in (7). After acetylation of the betulin hydroxyl groups, the olefin function of diacetate (2) is shifted to the thermodynamically more favourable position in (3) by rearrangement of carbocation intermediates. Subsequent oxidations then yield mono- and di-ketones (4) and (5). Finally, Baeyer-Villiger oxy-insertion of diketone (5) furnishes anhydride (6), whose olefin function is cleaved oxidatively with concomitant hydrolysis of the anhydride group to afford ketoacid (7). The chemical yields of the isolated products (2)-(7) were 96, 64, 100, 94, 95, and 51%, respectively. The cumulative yield for the overall transformation from (1) to (7) was thus ca. 28%. Only a single chromatographic step is required during the reaction sequence, i.e. purification of the final product (7).

The oxidative cleavage of anhydride (6) to ketoacid (7) has been reported, although no details were provided (Sarek, J.; Klinot, J.; Klinotova, E.; Sejbal, J. *Chemicke Listy* 1997, 11, 1005-1006): apparently, an ethyl acetate/water two-phase system with ruthenium (VIII) tetroxide ($RuO_4$), generated in situ from ruthenium(IV) oxide ($RuO_2$) with sodium periodate ($NaIO_4$), was adopted. Oxidative olefin cleavage with the aid of $RuO_4$ has been known for some time (Lee, D. G.; van den Engh, M. In *Oxidation in Organic Chemistry*. Trahanovsky, W. S., Ed. Academic Press: New York, 1973. Part B, Chapter 4). These reactions are usually carried out using a catalytic amount of $Ru_2O$, which is oxidised in the aqueous phase by $IO_4^-$ to $RuO_4$. The latter species is soluble in organic solvents and thus passes into the organic phase, where it oxidises the substrate and itself is reduced back to $Ru_2O$. Providing excess $IO_4^-$ in the aqueous phase thus ensures continuous regeneration of the reactive ruthenium species. However, we have observed this catalyst re-cycling reaction with (6) failing using various different commercial preparations of anhydrous $RuO_2$ or hydrates ($RuO_2.xH_2O$) and adopting aqueous two-phase systems with halogenated solvents or ethyl acetate. Exploratory experiments using homogeneous reaction in carbon tetrachloride with freshly prepared solutions of $RuO_4$ (preparation as described in: Fieser, L. F.; Fieser, M. *Reagents for Organic Synthesis*. John Wiley & Sons: New York, 1967. Vol. 1, p 986) have demonstrated that the oxidative olefin cleavage is feasible in principle but is difficult to drive to completion and various by-products were formed. Catalyst inactivation is frequently encountered in this reaction and incorporation of the water-miscible organic solvent acetonitrile into the standard carbon tetrachloride/water system in the ratio 2:2:3 MeCN/ $CCl_4/H_2O$) has been shown to alleviate this problem in many cases (Carlsen, P. H. J.; Katsuki, T.; Martin, V. S.; Sharpless, K. B. *J Org Chem*. 1981, 46, 3936-8). Using this system we have now observed the desired reaction on substrate (6) but conversion was still very sluggish and complex reaction mixtures were obtained. Substituting ethyl acetate for carbon tetrachloride and ruthenium (III) chloride ($RuCl_3$) for $RuO_2$ has resulted in both a more rapid and cleaner reaction; in particular, fewer polar impurities were formed under these conditions.

Accordingly, in a further aspect the present invention provides a process for the preparation of 3β,28-diacetoxy-18-oxo-19,20,21,29,30-pentanorlupan-22-oic acid (7) which comprises reacting the anhydride of 3β,28-diacetoxy-21,22-secolup-18-ene-21,22-dioic acid (6) with ruthenium (III) chloride and $NaIO_4$ in a MeCN/EtOAc/$H_2O$ solvent system and optionally converting the resultant 3β,0,28-diacetoxy-18-oxo-19,20,21,29,30-pentanorlupan-22-oic acid to 3β,28-diacetoxy-18-oxo-19,20,21,29,30-pentanorlupan-22-oic acid methanol solvate as described above.

Furthermore, a new purification regimen for the material obtained from the above process comprising: chromatographic separation ($SiO_2/CH_2Cl_2$ MeCN); washing with MeCN; and/or treatment with acetone has resulted in 3β,28-diacetoxy-18-oxo-19,20,21,29,30-pentanorlupan-22-oic acid (7) of >90% purity.

Accordingly, in a further aspect the present invention provides 3β,28-diacetoxy-18-oxo-19,20,21,29,30-pentanorlupan-22-oic acid in substantially pure form.

The term "substantially pure" as used herein in the context of 3β,28-diacetoxy-18-oxo-19,20,21,29,30-pentanorlupan-22-oic acid means material of >90% purity, preferably of >95% purity, more preferably of >97% purity, even more preferably of >99% purity.

Furthermore, material isolated from the new purification regimen may provide 3β,28-diacetoxy-18-oxo-19,20,21,29,30-pentanorlupan-22-oic acid acetonitrile solvate or 3β,28-diacetoxy-18-oxo-19,20,21,29,30-pentanorlupan-22-oic acid acetone solvate or a combination of solvates.

Accordingly, in a further aspect the present invention provides 3β,28-diacetoxy-18-oxo-19,20,21,29,30-pentanorlupan-22-oic acid acetonitrile solvate or 3β,28-diacetoxy-18-oxo-19,20,21,29,30-pentanorlupan-22-oic acid acetone solvate or a mixture thereof.

Furthermore, where the solvent used in the preparation of 3β,28-diacetoxy-18-oxo-19,20,21,29,30-pentanorlupan-22-oic acid is ethanol or iso-propanol or the like the corresponding solvates may be formed.

New solvates of 3β,28-diacetoxy-18-oxo-19,20,21,29,30-pentanorlupan-22-oic acid disclosed herein may possess one or more of the following advantages as compared to the non-solvated precursor: improved aqueous solubility, uniform size distribution, filtration and drying characteristics, stability (thermal or long term storage), flowability, handling characteristics, isolation and purification characteristics, physical properties advantageous to formulatory requirements e.g. compressibility.

Oxidation of (3) with chromium (VI) oxide (chromic anhydride, $CrO_3$) in aqueous acetic acid at room temperature for 12 h was reported (Sejbal, J.; Klinot, J.; Budesinsky, M.; Protiva, J. *Collect. Czech Chem. Commun.* 1991, 56, 2936-2949). A mixture of products was obtained from which ketone (4) was isolated in 30% yield after chromatography. We have found that superior results are obtained if the oxidation is carried out with a slight molar excess of sodium dichromate ($Na_2Cr_2O_7$) in a toluene/acetic acid/acetic anhydride solvent system containing sodium acetate at 60° C. Under these conditions crude ketone (4), suitable for further transformation, is obtained in quantitative yield after partitioning of the reaction mixture between water and ethyl acetate, followed by further washing of the organic fraction, drying, and evaporating. Furthermore, pure (4) could readily be obtained without recourse to chromatography simply by crystallisation from methanol. This procedure yields (4) of higher purity than previously reported (m.p. 207-208 versus 198-201° C. in Seijbal et al. cited above).

Thus, in a further aspect the present invention provides a process for the preparation of 21-oxo-lup-18-ene-3β,28-diyl diacetate (4) which comprises reacting lup-18-ene-3β,28-diyl diacetate (3) with sodium dichromate ($Na_2Cr_2O_7$) and sodium acetate wherein the sodium dichromate ($Na_2Cr_2O_7$) is present in a slight molar excess. Preferably the reaction is carried out in a toluene/acetic acid/acetic anhydride solvent system. Preferably the reaction is carried out at elevated temperature, more preferably at about 60° C.

The present invention also provides a process for the preparation of 3β,28-diacetoxy-18-oxo-19,20,21,29,30-pentanorlupan-22-oic acid (7) which comprises oxidising lup-18-ene-3β,28-diyl diacetate (3) with a slight molar excess of sodium dichromate ($Na_2Cr_2O_7$) as described above and converting the resultant 21-oxo-lup-18-ene-3β,28-diyl diacetate (4) to 3β,28-diacetoxy-18-oxo-19,20,21,29,30-pentanorlupan-22-oic acid (7) as described above and optionally converting the 3β,28-diacetoxy-18-oxo-19,20,21,29,30-pentanorlupan-22-oic acid to 3β,28-diacetoxy-18-oxo-19,20,21,29,30-pentanorlupan-22-oic acid methanol solvate.

Acid-catalysed isomerisation of (2) to (3) has been described (Suokas, E.; Hase, T. *Acta Chem. Scand. B* 1975, 29, 139-140). A system consisting of hydrobromic acid, acetic acid, and acetic anhydride in benzene was employed and a correlation in terms of formation of (3) between reaction time and HBr concentration was noted. Performing the reactions at ambient temperature, optimal yields (70-87%) of (3) were reported with reaction times of 18 h to (2) weeks, depending on acid strength (1.1-1.6 M HBr). Similar results were reported elsewhere (Sejbal, J.; Klinot, J.; Vystrcil, A. Collect. *Czech Chem. Commun*. 1987, 52, 487-492). We have found that elevated reaction temperatures permit shortening of the reaction time. Thus at 90° C., the optimal temperature found, reaction times of 2-4 h are sufficient to achieve complete conversion of (2) with >70% content of (3) in the product (by NMR analysis of crude reaction product after evaporation of solvents). At this temperature, an HBr concentration of 0.9 M was found optimal (using 2.6 M $Ac_2O$ and ca. 4 M AcOH in toluene); small deviations in HBr concentration in either direction led to significantly lower yields. In this system a substrate (2) concentration of ca. 0.24 M can be achieved while maintaining a homogeneous reaction. The most effective solvent for the crystallisation from evaporation residues and recrystallisation of (3) was found to be ethyl acetate; employment of this isolation solvent obviates chromatographic purification.

Thus, in a further aspect the present invention provides a process for the preparation of lup-18-ene-3β,28-diyl diacetate (3) which comprises isomerizing lup-20(29)-ene-3β,28-diyl diacetate (2) in a benzene/acetic acid/acetic anhydride solvent system at elevated temperature wherein the concentration of HBr is between about 0.8 and about 1.0M, preferably between about 0.85 and about 0.95M, most preferably about 0.9M. Preferably the reaction is carried out at about 90° C.

In a further aspect the present invention also provides a process for isolating and/or purifying lup-18-ene-3β,28-diyl diacetate (3) which comprises crystallising or recrystallising crude lup-18-ene-3β,28-diyl diacetate (3) from ethyl acetate.

Betulin (1) is a pentacyclic triterpene isolated from birch bark (for review, see, e.g., Hayek, E. W. H.; Jordis, U.; Moche, W.; Sauter, F. *Phytochem*. 1989, 28, 2229-2242). It can be acetylated to afford the diacetate (2) as described (see, e.g., Tietze, L. F.; Heinzen, H.; Moyna, P.; Rischer, M.; Neunaber, H. *Liebigs Ann. Chem*. 1991, 1245-1249). We have found that the reaction yield of (2) is highly dependent on the quality of betulin (1) employed. Thus material of >97% purity permits practically quantitative yields of (2), while application of lower grade (1), e.g. commercial materials with purity of <95%, results in <75% yields of (2). Betulin (1) can be purified chromatographically or by recrystallisation from various solvent systems (see, e.g., Eckerman, C.; Ekman, R. *Paperi ja Puu* 1985, 67(3), 100-106). We have found that diacetate (2) can be isolated by precipitation from methanol after evaporation of the acetylation reaction mixture. Material thus isolated is suitable for direct application in the next reaction step.

Thus in a further aspect the present invention provides a (commercial) process for the preparation of lup-20(29)-ene-3β,28-diyl diacetate (2) which comprises reacting substantially pure betulin with acetic anhydride and a base, preferably pyridine, and isolating the crude product by precipitation from methanol.

In a further aspect the present invention also provides the use of substantially pure betulin for the (commercial) manufacture of 3β,28-diacetoxy-18-oxo-19,20,21,29,30-pentanorlupan-22-oic acid (7) and/or 3β,28-diacetoxy-18-oxo-19,20,21,29,30-pentanorlupan-22-oic acid methanol solvate.

The term "substantially pure betulin" as used herein means material of >95% purity, preferably of >97%, more preferably of >99% purity i.e. betulin having respectively less than 5%, preferably less than 3%, more preferably less than 1% of non-betulin material present.

The present invention is further described by way of example.

EXAMPLES

Nomenclature

The compounds are named as derivatives of the natural product lupane and the numbering convention for the C atoms is as follows:

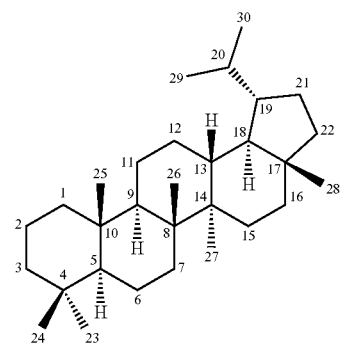

General

M.p. were determined using a Reichert (model 7905) hot stage apparatus and are uncorrected. HPLC-MS was performed using a Waters 2695 HPLC system fitted with a Waters 996 PDA (photodiode array) detector and a Micromass ZMD mass spectrometer (HPLC conditions: column: Jupiter 250×4.6 mm, $C_4$ stationary phase, (5) μm particles, 300 Å pores; T=30° C. (column) and 10° C. (sample compartment); flow rate: (1) mL/min, injection volume: 20 μL; detectors: λ=191-300 nm, mass range m/z=100-1000; mobile phase A: 0.1% $CF_3CCOH$ in $H_2O$, B: 0.1% $CF_3COOH$ in MeCN; elution with linear gradient from 0 to 100% B in A over 10 min, followed by isocratic elution with 100% B). GLC was carried out on an Agilent 6850A series gas chromatogram (GLC conditions: column: HP-5 (5% phenyl methyl siloxane) length 30 m, diameter 250 μm, 0.25 μm film thickness; inlet T=350° C.; split ratio=50:1; split flow=52 mL/min; total flow=56 mL/min; He carrier gas; oven T (isocratic)=300° C.; run time=30 min; detector: FID, T=350° C.; H flow=30 mL/min, air flow=400 mL/min; make-up gas/flow=He, 45 mL/min). Mass spectra for lup-20(29)-ene-3β,28-diyl diacetate and lup-18-ene-3β,28-diyl diacetate were recorded on a Micromass Trio 2000 spectrometer fitted with a quadrupole detector (Dept. Chemistry, University of Manchester, England). $^1$H-NMR spectra were obtained using a Varian Unity INOVA 400 FT spectrometer. $^{13}$C-NMR spectra were recorded using a Bruker AC-250 FT-NMR spectrometer (62.5 MHz). Chemical shifts are reported in p.p.m. ($\delta$) relative to SiMe$_4$. FT-IR spectra were obtained from solid samples (using a 'golden gate' sample presentation unit) on a Bruker Vector 22 spectrophotometer. Optical rotations were measured on a POLAAR 2001 polarimeter. TLC was carried out using aluminium plates coated with silica gel 60 F$_{254}$ (Merck) using molybdate stain for all products and UV (254 nm) visualisation where appropriate. For the stain: (NH$_4$)$_2$MoO$_4$ (50 g), Ce$_2$(SO$_4$)$_3$ (3 g), H$_2$O (950 ml), conc. H$_2$SO$_4$ (50 mL). Plates were dipped and heated with a hot air gun to develop. All products stained dark blue. Purification of 3$\beta$,28-diacetoxy-18-oxo-19,20,21,29,30-pentanorlupan-22-oic acid was carried out using Matrex Silica 60 (code S/0683/60, supplied by Fisher Scientific). Elemental microanalyses (C, H) were carried out by Butterworth Laboratories Ltd., Teddington, Middlesex, England.

Lup-20(29)-ene-3$\beta$,28-diyl Diacetate (2)

A solution of pyridine (150 mL, 1.86 mol) and Ac$_2$O (150 mL, 1.59 mol) was heated and stirred at 80° C. (oil bath). Betulin (1) (98%; 280.9 g, 0.634 mol) was added in portions (20-30 g/portion), allowing complete dissolution between additions. About 15 min after complete addition the reaction mixture solidified (bath temperature 95° C.). Upon further heating the solid had almost dissolved. More pyridine and Ac$_2$O (20 mL each) were added and the reaction mixture was heated under reflux for 1 h. The mixture was cooled for 5 min (once again solidification was observed), the solvents were evaporated and MeOH (0.5 L) was added. The solid was divided by sonication and manual crushing, then filtered, washed with MeOH (2 L), and dried on the sinter. The filter cake was dried in vaccuo to afford (2) (320 g, 96%) as a white amorphous solid, containing only trace amounts of impurities by TLC and $^1$H-NMR analysis. An analytical sample was prepared by dry flash chromatography (10-20% EtOAc/isohexane), followed by recrystallising twice from EtOH. TLC (Et$_2$O): R$_F$=0.7 (homogeneous). GLC: t$_R$=17.4 min (92.6%). EI-MS: m/z=466 (75%), 526 (M+; ~(5) %); C$_{34}$H$_{54}$O$_4$=526. Found C 77.54 (77.52), H 10.30 (10.33). M.p. 223-225° C. [$\alpha$]$_D$=+21° (c 5.233, CHCl$_3$). $^1$H-NMR (CDCl$_3$) $\delta$ inter alii: 0.85 (s, 3H CH$_3$), 0.85 (s, 6H, CH$_3$), 0.98 (s, 3H, CH$_3$), 1.05 (s, 6H, CH$_3$), 1.70 (s, 3H CH$_3$), 2.45 (ddd, 1H, C$^{19}$H), 3.87 (d, 1H, J=11 Hz, C$^{28}$H$^\alpha$), 4.26 (dd, 1H, J=11 Hz, C$^{28}$H$^\beta$), 4.48 (m, 1H, C$^3$H$^\alpha$), 4.61 (m, 1H, C$^{21}$H$^E$), 4.70 (m, 1H, C$^{21}$H$^Z$). $^{13}$C-NMR (CDCl$_3$) $\delta$ inter alii: 171.5, 170.9, 150.0, 149.7, 109.9, 80.9 (C$^3$). FT-IR: 1729 cm$^{-1}$ (ROCOMe).

Lup-18-ene-3$\beta$,28-diyl Diacetate (3)

A solution of HBr in AcOH (Aldrich, 24,863-0; 30 wt. %; 90 mL) was added to a solution of (2) (45.03 g, 85.48 mmol) in PhMe (90 mL), Ac$_2$O (90 mL), and AcOH (90 mL) at 90° C. The mixture was stirred and heated at this temperature for 4 h. After cooling, NaOAc (45 g) was added and the mixture was evaporated to dryness. The residue was re-evaporated from MeOH (40 mL), the residue was triturated with MeOH, filtered, and washed copiously with more MeOH. The resulting solid was dissolved in hot EtOAc (~0.7 L), cooled on ice for 1.25 h, filtered, washed (MeOH then isohexane), and dried. A further recrystallisation from hot EtOAc (~0.7 L) afforded pure title compound (3) (28.9 g, 64%) as colourless needles. GLC: t$_R$=15.8 min (99.4%). EI-MS: m/z=453 (100%), 526 (M+; ~27%); C$_{34}$H$_{54}$O$_4$=526. Found C 77.11 (77.52), H 10.20 (10.33). M.p. 214-215° C. [$\alpha$]$_D$=+17° (c 4.582, CHCl$_3$). $^1$H-NMR (CDCl$_3$) $\delta$ inter alii: 0.85 (s, 3H CH$_3$), 0.86 (s, 3H, CH$_3$), 0.90 (s, 3H, CH$_3$), 0.91 (s, 3H, CH$_3$), 0.92 (d, 3H, CH$_3$), 1.00 (d, 3H, CH$_3$), 1.07 (s, 3H, CH$_3$), 2.05 (s, 3H, OCOCH$_3$), 2.06 (s, 3H, OCOCH$_3$), 2.25 (m, 2H), 2.44 (m, 1H), 3.15, (sept, 1H, C$^{20}$H), 4.01 (m, 2H, C$^{28}$H$_2$), 4.50 (m, 1H, C$^3$H$^\alpha$). $^{13}$C-NMR (CDCl$_3$) $\delta$ inter alii: 171.5, 171.0, 143.6, 134.0, 80.9 (C$^3$). FT-IR: 1736 cm$^{-1}$ (2 stretches, ROCOMe).

21-Oxo-lup-18-ene-3$\beta$,28-diyl Diacetate (4)

A mixture of (3) (63.4 g, 121 mmol), NaOAc (56.8 g, 693 mmol), PhMe (0.8 L), AcOH (1 L), Ac$_2$O (220 mL), and Na$_2$Cr$_2$O$_7$.2H$_2$O (Aldrich 39,806-3, 99.5+%; 42.6 g, 143 mmol) was stirred and heated at 60° C. overnight. After cooling, H$_2$O (1.4 L) and EtOAc (1 L) were added and the phases were separated. The organic phase was washed successively with H$_2$O (1 L), saturated aq Na$_2$CO$_3$ (3×0.8 L), H$_2$O (1 L), and brine (3×0.7 L). It was dried over MgSO$_4$, filtered, and evaporated to afford crude (4) (68 g, ~quant.). TLC (EtOAc/isohexane, 1:4): Rf=0.25 (homogeneous). A sample was purified for analysis by crystallisation from hot MeOH with 65% recovery. GLC: t$_R$=23.8 min (97.9%). HPLC-MS: m/z=541 (M+1); C$_{34}$H$_{52}$O$_5$=540. Found C 75.21 (75.51), H 9.57 (9.69). M.p. 207-208° C. [$\alpha$]$_D$=−35° (c 4.755, CHCl$_3$). $^1$H-NMR (CDCl$_3$) $\delta$ inter alii: 0.85 (s, 3H, CH$_3$) 0.86 (s, 3H, CH$_3$), 0.93 (s, 3H, CH$_3$), 0.94 (s, 3H, CH$_3$), 1.16 (s, 3H, CH$_3$), 1.17 (d, 3H, J=(7).1 Hz, CH$_3$), 1.95 (d, 1H, J=18 Hz, C$^{22}$H$^\alpha$), 2.00 (s, 3H, OCOCH$_3$), 2.05 (s, 3H, OCOCH$_3$), 2.39 (d, 1H, J=18 Hz, C$^{22}$H$^\beta$), 2.87 (dd, 1H, J'=11.9 Hz, J"=4.1 Hz, C$^{13}$H$^\beta$), 3.18 (sept., 1H, J=(6).6, C$^{20}$H); 4.06 (d, 1H, J=10.9 Hz, C$^{28}$H$^\alpha$); 4.34 (d, 1H, J=10.9 Hz, C$^{28}$H$^\beta$), 4.49 (m, 1H, J=(7) Hz, C$^3$H$^\alpha$). $^{13}$C-NMR (CDCl$_3$) $\delta$ inter alii: 207.9 (C$^{21}$), 171.8, 171.0, 170.9, 146.8, 80.7. (C$^3$). FT-IR: 1734 cm$^{-1}$ (ROCOMe), 1694 cm$^{-1}$ ($\alpha$,$\beta$-unsaturated ketone).

21,22-Dioxo-lup-18-ene-3$\beta$,28-diyl Diacetate (5)

Ketone (4) (20 g, 37 mmol) was dissolved in dioxane (100 mL) and SeO$_2$ (Aldrich 21,336-5, 99.8%; 5 g, 45 mmol) was added. The mixture was heated to reflux for 2 h. After cooling, it was filtered through a pad of Celite. The filtrate was poured slowly into stirred H$_2$O (0.3 L) and the pink solid precipitate was filtered and washed with H$_2$O (100 mL). The product was dried to afford (5) (19.2 g, 94%) as a peach-coloured crystalline solid. A sample was purified for analysis by crystallisation from EtOH. HPLC-MS: t$_R$=14.00 min; m/z=555 (M+1); C$_{34}$H$_{50}$O$_6$=554. Found C 73.30 (73.61), H 9.03 (9.08). M.p. 271-275° C. [$\alpha$]$_D$=−128° (c 5.040, CHCl$_3$). $^1$H-NMR (CDCl$_3$) $\delta$ inter alii: 0.85 (s, 3H, CH$_3$), 0.86 (s, 3H, CH$_3$), 0.94 (s, 3H, CH$_3$), 0.97 (s, 3H, CH$_3$), 1.18 (s, 3H, CH$_3$), 1.24 (d, 3H, J=(7).2 Hz, CH$_3$), 1.26 (d, 3H, J=(7).2 Hz, CH$_3$), 1.93 (s, 3H, OCOCH$_3$), 2.06 (s, 3H, OCOCH$_3$), 3.12 (dd, 1H, J'=12.5 Hz, J"=3.8 Hz, C$^{13}$H$^\beta$), 3.36 (sept., 1H, J=(7) Hz, C$^{20}$H); 4.02 (d, 1H, J=11.1 Hz, C$^{28}$H$^\alpha$), 4.49 (dd, 1H, J'=10.2 Hz, J"=(6).0 Hz, C$^3$H$^\alpha$), 4.86 (d, 1H, J=11.1, C$^{28}$H$^\beta$). $^{13}$C-NMR (CDCl$_3$) $\delta$ inter alii: 200.9, 189.4, 171.1, 170.9, 170.1, 152.3, 80.6 (C$^3$). FT-IR: 1763, 1745, 1733, 1702 cm$^{-1}$ (diketone, (2) ROCOMe, $\alpha$,$\beta$-unsaturated ketone).

Anhydride of 3$\beta$,28-diacetoxy-21,22-secolup-18-ene-21,22-dioic Acid (6)

Diketone (5) (110 g, 199 mmol) was dissolved in CHCl$_3$ (350 mL) and peracetic acid (36-40 wt. % in AcOH; 500 mL) was added. The mixture was stirred rapidly overnight to afford a colourless mixture. This was diluted with CHCl$_3$ (0.5 L) and H$_2$O (1 L); the organic layer was separated and was washed with saturated aq NaHCO$_3$ solution (2×0.7 L), H$_2$O (0.5 L) and brine (0.5 L). It was dried over MgSO$_4$, filtered, and evaporated until formation of solids started. MeOH (1 L) was added and the resulting white solid was collected by filtration. The filter cake was washed with MeOH (0.2 L) and dried to afford (6) (107.6 g, 95%) as a white crystalline solid. An analytical sample was prepared by crystallising 1.5 g of this material twice from CHCl$_3$ (recovery 530 mg). HPLC-MS: $t_R$=10.90 min; m/z=571 (M+1, ~10%), 529 (100%), 588 (M+18, ~30%); C$_{34}$H$_{50}$O$_7$=570. Found C 70.86 (71.55), H 8.55 (8.83). M.p. 269-273° C. $[\alpha]_D$=+97° (c 4.911, CHCl$_3$). $^1$H-NMR (CDCl$_3$) δ inter alii: 0.85 (s, 3H, CH$_3$), 0.85 (s, 3H, CH$_3$), 0.90 (s, 3H, CH$_3$), 0.91 (s, 3H, CH$_3$), 1.11 (s, 3H, CH$_3$), 1.14 (d, 3H, J=(7) Hz, CH$_3$), 1.31 (d, 3H, J=(7) Hz, CH$_3$), 2.01 (s, 3H, OCOCH$_3$), 2.05 (s, 3H, OCOCH$_3$), 2.53 (dt, 1H, J'=14.4 Hz, J"=3.5 Hz), 2.72 (dd, 1H, J'=3.1 Hz, J"=12.3 Hz), 3.26 (sept., 1H, J=(7) Hz, C$^{20}$ H), 3.90 (d, 1H, J=11.0 Hz, C$^{28}$H$_2$), 4.54 (d, 1H, J=11.0 Hz, C$^{28}$H$_2$), 4.47 (m, 1H, C$^3$H). $^{13}$C-NMR (CDCl$_3$) δ inter alii: 170.9, 170.1, 169.8, 159.3, 151.6, 135.4, 80.5 (C$^3$). FT-IR: 1783, 1739, 1717, 1620 cm$^{-1}$ (anhydride, (2) ROCOMe, α,β-unsaturated anhydride).

3β,28-Diacetoxy-18-oxo-19,20,21,29,30-pentanorlupan-22-oic Acid (7)

Anhydride (6) (100 g, 175 mmol), RuCl$_3$.H$_2$O (Lancaster, 0421, Ru content ~40%; 25 g, ~99 mmol), MeCN (4.2 L), EtOAc (4.2 L), and H$_2$O (6 L) were combined and the resulting solution was stirred mechanically. NaIO$_4$ (Aldrich, 21,004-8, 99%; 0.5 kg, 2.34 mol) was added and the mixture was stirred vigorously overnight. More NaIO$_4$ (150 g 0.7 mol) was added the following morning when the reaction had quenched (ruthenium catalyst had precipitated as insoluble RuO$_2$, the organic layer was colourless and no 03 odour could be detected) and another portion (150 g) before being again stirred overnight. A final portion of NaIO$_4$ (150 g) was added the following morning and stirring was continued for a further 24 h. TLC analysis of the organic layer (plate pre-dipped/evaporated in eluent (CH$_2$Cl$_2$/MeCN/AcOH, 80:20:1) at this point indicated mostly the desired product ($R_F$~0.35) with a small amount of starting material ($R_F$~0.85) and some impurities ($R_F$~0.25). The mixture was filtered and the filter cake was washed with EtOAc/MeCN (1 L) and H$_2$O (0.5 L). The filtrate and washings were combined and the organic phase was separated. This was washed successively with H$_2$O (4 L) and brine (4 L), dried (MgSO$_4$), and evaporated. The residue was evaporated from PhMe (3×0.5 L) and was finally dried under high vacuum to afford the crude title compound (7) (91 g). This material was chromatographed (1.1 kg SiO$_2$; 10.5 cm diameter column) by gravity elution with CH$_2$Cl$_2$ followed by MeCN/CH$_2$Cl$_2$ (5-20%, 1-L fractions). The fractions containing pure product were combined and evaporated to the on-set of crystallisation. The white crystals were filtered, washed with MeCN (~50 mL), air-dried on the sinter, and high-vacuum dried for 2 h. This material (49 g, 55%) was treated with Me$_2$CO (0.8 L), filtered, and dried to afford pure (7) as a white powder (45 g, 51%). HPLC-MS: $t_R$=13.13 min; m/z=505 (M+1), 522 (M+18); C$_{29}$H$_{44}$O$_7$=504. Found C 68.37 (69.02), H 8.84 (8.79). M.p. 142-144° C. $[\alpha]_D$=+45° (c 3.73 CHCl$_3$). $^1$H-NMR (CDCl$_3$, 400 MHz) δ inter alii: 0.85 (s, 3H, CH$_3$), 0.86 (s, 3H, CH$_3$), 0.90 (s, 3H, CH$_3$), 0.91 (s, 3H, CH$_3$), 1.14 (s, 3H, CH$_3$), 2.04 (s, 3H, OCOCH$_3$), 2.05 (s, 3H, OCOCH$_3$), 2.19-2.25 (m, 2H), 2.85 (dd, 1H, J'=3.5 Hz, J"=11.8 Hz, C$^{13}$H); 4.43 (d, 1H, J=11.1 Hz, C$^{28}$H$_2$), 4.46-4.50 (m, 1H, C$^3$H$^\alpha$), 4.71 (d, 1H, J=11.1 Hz, C$^{28}$H$_2$).

$^{13}$C-NMR (CDCl$_3$, 100.5 MHz) δ 214.9(COOH); 173.6, 171.0, 170.5 (CO); 58.1, 47.0, 41.1, 37.8, 37.1 (quat. C); 80.6, 55.5, 50.6, 49.9 (CH); 66.0, 38.5, 34.0, 28.9, 26.9, 23.5, 21.7, 19.6, 18.1 (CH$_2$); 27.9, 21.3, 20.6, 16.7, 16.5, 16.3, 16.1 (CH3). FT-IR: 1748, 1716 cm$^{-1}$ (ROCOMe and saturated ketone).

3β,28-diacetoxy-18-oxo-19,20,21,29,30-pentanorlupan-22-oic acid (7) (ca. 20 mg) was dissolved in 2 mL of CHCl$_3$/EtOAc (1:1, v/v). The solution was filtered and the filtrate was concentrated to half the original volume. An open-top vial containing this solution was then placed into a larger container charged with a mixture of petroleum spirit (40-60° C. fraction) and methanol (ca. 5:1, v/v). The outer container was sealed and allowed to stand at ambient temperature (ca. 23° C.). After 3 days crystals had formed as colourless needles of 3β,28-diacetoxy-18-oxo-19,20,21,29, 30-pentanorlupan-22-oic acid•1.5 MeOH. These were used for X-ray crystal structure analysis.

Figure 2:
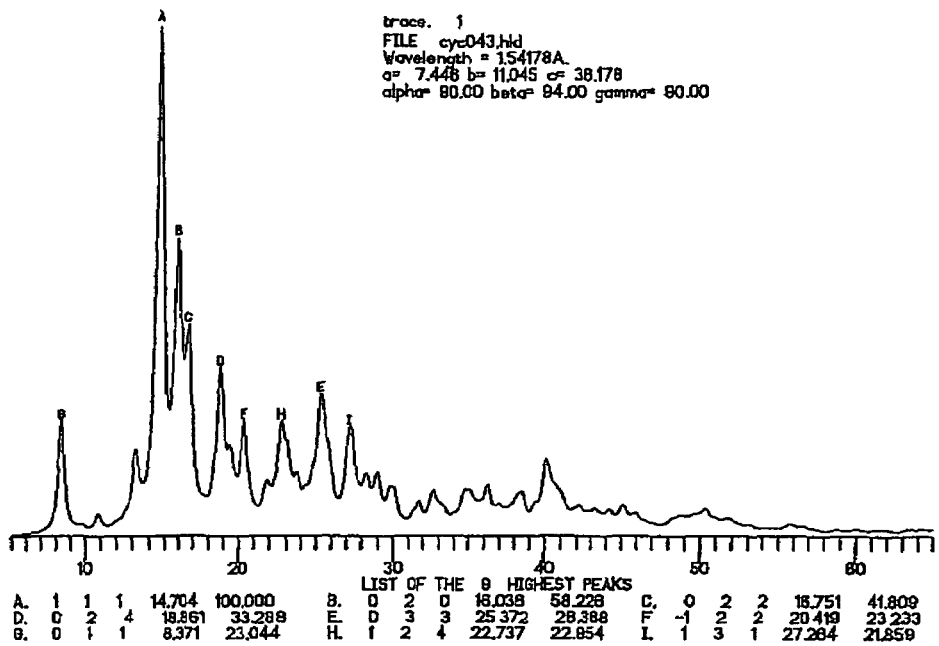
FIG. 2 shows the powder X-ray diffraction pattern of 3β,28-diacetoxy-18-oxo-19,20,21,29,30-pentanorlupan-22-oic acid•1.5MeOH calculated assuming low and high resolution conditions.
Figure 2:
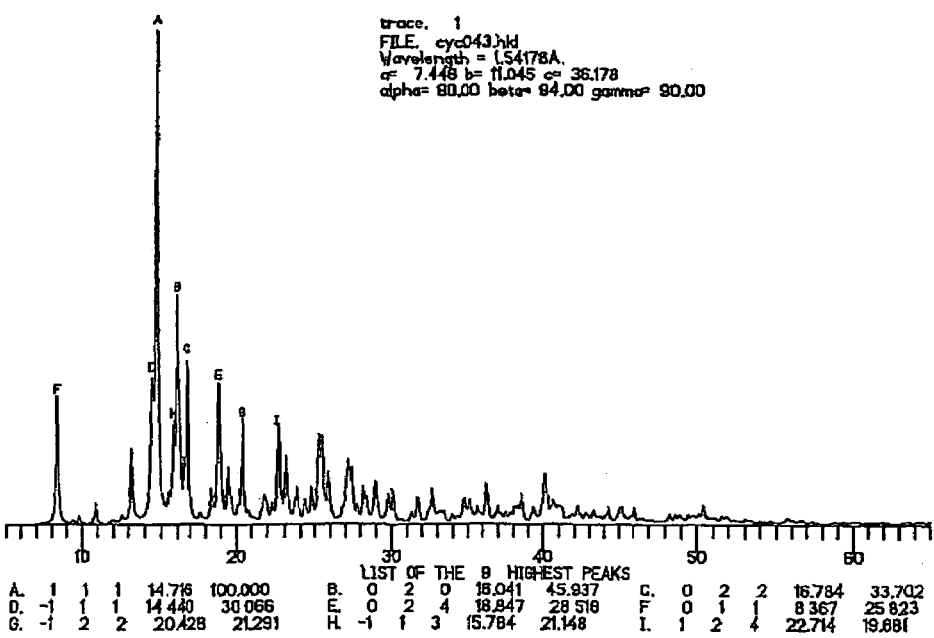

Crystal structure determination of 3β,28-diacetoxy-18-oxo-19,20,21,29,30-pentanorlupan-22-oic Acid•1.5MeOH Single crystals of 3β,28-diacetoxy-18-oxo-19,20,21,29, 30-pentanorlupan-22-oic acid•1.5MeOH were prepared as described above. Diffraction data were collected on a Stoe Stadi-4 diffractometer equipped with an Oxford Cryosystems low-temperature device operating at 150 K. An absorption correction was applied by Gaussian integration following optimisation of the crystal shape and dimensions against Ψ-scan data. The six most enantiosensitive reflections were 120; 146; 22,10; 14,15; 150 and 224. These, their Laue equivalents and their Friedel opposites were re-measured at opposing values of 2θ extremely carefully and included in the data set used for refinement. A set of crystal data is shown in Table 1. The structure was solved by direct methods and refined by full-matrix least-squares against F$^2$ (SHELXTL), to reveal an asymmetric unit consisting of two molecules of (7) and three molecules of methanol of solvation. One carboxylic acid group is disordered via a two-fold rotation about the C—C bond. H-atoms were placed in ideal positions and allowed to ride on their parent atoms. All non-H atoms were refined with anisotropic displacement parameters to yield a final conventional R-factor of 3.63%. Refinement with statistical weights [w=1/σ$^2$(F$^2$)] gave a final Flack parameter of −0.05(9). The signs of the observed and calculated Bijvoet differences were the same for all six sensitive reflections. Taken with the known chiral purity of the sample (refer chromatographic and spectroscopic data above), these data confirm the absolute structure of (7) as shown. The chemical connectivity of (7) was clearly established to be as proposed. The structures of the two independent molecules (FIG. 1) do not differ, except for the disorder in one of the carboxyl groups. In addition to (7) there are three crystallographically independent molecules of methanol of solvation; packing is dominated by H-bond formation between these and the carboxyl groups of the (7) molecules. Bond lengths and angles adopt normal values Table 3; H-bond parameters are listed in Table 6; atomic coordinates are given in Table 2; anisotropic displacement parameters are listed in Table 4; and hydrogen coordinates (×10$^4$) and isotropic displacement parameters are set out in Table 5. The powder diffraction pattern for (7) was calculated from the cell parameters and intensity data collected during this single crystal study. A plot of this is shown in FIG. 2.

TABLE 1

Crystal data and structure refinement for 3β,28-diacetoxy-18-oxo-19,20,21,29,30-pentanorlupan-22-oic acid (7).

A. CRYSTAL DATA

| | |
|---|---|
| Empirical formula | $C_{30.50}H_{50}O_{8.50}$ ($C_{29}H_{44}O_7 \cdot 1.5$MeOH) |
| Formula weight | 552.70 |
| Wavelength | 1.54178 Å |
| Temperature | 150(2) K |
| Crystal system | Monoclinic |
| Space group | $P2_1$ |
| Unit cell dimensions | a = 7.4459(9) Å, α = 90 ° |
| | b = 11.0454(9) Å, β = 94.002(11) ° |
| | c = 36.178(4) Å, γ = 90 ° |
| Volume | 2968.2(5) Å$^3$ |
| Number of reflections for cell | 86 (20 < θ < 22 °) |
| Z | 4 |
| Density (calculated) | 1.237 Mg/m$^3$ |
| Absorption coefficient | 0.722 mm$^{-1}$ |
| F(000) | 1204 |

B. DATA COLLECTION

| | |
|---|---|
| Crystal description | Colourless block |
| Crystal size | 0.64 × 0.32 × 0.27 mm |
| Instrument | Stoe Stadi-4 |
| θ range for data collection | 3.67 to 69.75 ° |
| Index ranges | −8 ≤ h ≤ 8, −13 ≤ k ≤ 13, 0 ≤ l ≤ 43 |
| Reflections collected | 10322 |
| Independent reflections | 10322 [R$_{(int)}$ = 0.0000] |
| Scan type | ω-2θ' |
| Absorption correction | Optimised numerical (T$_{min}$ = 0.719, T$_{max}$ = 0.890) |

C. SOLUTION AND REFINEMENT

| | |
|---|---|
| Solution | direct (SHELXS-97 (Sheldrick, 1990)) |
| Refinement type | Full-matrix least-squares on F$^2$ |
| Program used for refinement | SHELXL-97 |
| Hydrogen atom placement | geom. |
| Hydrogen atom treatment | riding |
| Data/restraints/parameters | 10322/7/751 |
| Goodness-of-fit on F$^2$ | 1.054 |
| Conventional R [F > 4σ(F)] | R1 = 0.0363 [9821 data] |
| Weighted R (F$^2$ and all data) | wR2 = 0.1009 |
| Absolute structure parameter | −0.05(9) |
| Extinction coefficient | 0.00226(12) |
| Final maximum δ/σ | 0.008 |
| Weighting scheme | calc w = 1/[s2 (F$_o^2$) + (0.0557 P)$^2$ 0.7729 P] where P = (F$_o^2$ + 2 F$_c^2$)/3 |
| Largest diff. peak and hole | 0.247 and −0.191 e.Å$^{-3}$ |

TABLE 2

Atomic coordinates (×10$^4$), equivalent isotropic displacement parameters (Å$^2$ × 10$^3$) and site occupancies. U(eq) is defined as one third of the trace of the orthogonalized U$_{ij}$ tensor.

| Atom | x | y | z | U(eq) | Occ |
|---|---|---|---|---|---|
| O11 | 5250(2) | 1190(2) | −1514(1) | 48(1) | 1 |
| C11 | 6696(3) | 1412(2) | −1356(1) | 33(1) | 1 |
| C211 | 8952(3) | 2392(2) | −1719(1) | 46(1) | 1 |
| O221 | 10561(2) | 2195(2) | −1913(1) | 48(1) | 1 |
| O231 | 10804(3) | 4195(2) | −1991(1) | 58(1) | 1 |
| C231 | 11371(3) | 3183(2) | −2038(1) | 42(1) | 1 |
| C241 | 13009(3) | 2848(3) | −2231(1) | 53(1) | 1 |
| C21 | 8442(3) | 1186(2) | −1553(1) | 35(1) | 1 |
| C251 | 8000(5) | 66(7) | −1820(2) | 36(1) | 0.67(2) |
| O261 | 7639(5) | 431(7) | −2162(1) | 52(2) | 0.67(2) |
| O271 | 7952(5) | −967(5) | −1718(2) | 55(1) | 0.67(2) |
| C25'1 | 7869(11) | 585(11) | −1923(3) | 29(2) | 0.33(2) |
| O26'1 | 7977(9) | −590(10) | −1874(4) | 39(2) | 0.33(2) |
| O27'1 | 7362(11) | 1098(12) | −2210(2) | 58(2) | 0.33(2) |
| C31 | 9967(2) | 696(2) | −1283(1) | 30(1) | 1 |
| C41 | 10054(2) | 1313(2) | −905(1) | 26(1) | 1 |
| C51 | 8259(2) | 1248(2) | −718(1) | 21(1) | 1 |
| C511 | 7677(2) | −96(2) | −705(1) | 28(1) | 1 |
| C61 | 8406(2) | 1846(1) | −318(1) | 21(1) | 1 |
| C611 | 9263(2) | 3110(2) | −340(1) | 29(1) | 1 |
| C71 | 9628(2) | 1064(2) | −55(1) | 25(1) | 1 |
| C81 | 9595(2) | 1417(2) | 353(1) | 26(1) | 1 |
| C91 | 7677(2) | 1318(2) | 477(1) | 21(1) | 1 |
| C101 | 7582(2) | 1263(2) | 907(1) | 25(1) | 1 |
| C1011 | 8596(3) | 137(2) | 1057(1) | 35(1) | 1 |
| C1021 | 8394(2) | 2366(2) | 1115(1) | 32(1) | 1 |
| C111 | 5587(2) | 1076(2) | 978(1) | 26(1) | 1 |
| O1111 | 5393(2) | 1160(1) | 1374(1) | 30(1) | 1 |
| O1121 | 3315(3) | −310(2) | 1339(1) | 63(1) | 1 |
| C1121 | 4163(3) | 449(2) | 1516(1) | 37(1) | 1 |
| C1131 | 3923(4) | 752(3) | 1913(1) | 57(1) | 1 |
| C121 | 4322(2) | 1989(2) | 788(1) | 28(1) | 1 |
| C131 | 4472(2) | 1974(2) | 368(1) | 26(1) | 1 |
| C141 | 6407(2) | 2224(1) | 257(1) | 21(1) | 1 |
| C1411 | 6825(2) | 3569(2) | 344(1) | 29(1) | 1 |
| C151 | 6488(2) | 1907(2) | −164(1) | 21(1) | 1 |
| C161 | 5208(2) | 2649(2) | −427(1) | 30(1) | 1 |
| C171 | 5024(2) | 2085(2) | −812(1) | 31(1) | 1 |
| C181 | 6858(2) | 1966(2) | −973(1) | 26(1) | 1 |
| O12 | 4532(2) | 622(2) | 6504(1) | 52(1) | 1 |
| C12 | 3111(2) | 895(2) | 6342(1) | 32(1) | 1 |
| C22 | 1326(2) | 684(2) | 6528(1) | 30(1) | 1 |
| C212 | 829(3) | 1916(2) | 6689(1) | 36(1) | 1 |
| O222 | −916(2) | 1790(1) | 6831(1) | 47(1) | 1 |
| O232 | −485(3) | 3521(2) | 7128(1) | 91(1) | 1 |
| C232 | −1458(3) | 2697(2) | 7037(1) | 46(1) | 1 |
| C242 | −3338(4) | 2521(3) | 7142(1) | 72(1) | 1 |
| C252 | 1718(2) | −292(2) | 6828(1) | 37(1) | 1 |
| O262 | 2044(2) | 156(2) | 7163(1) | 52(1) | 1 |
| O272 | 1751(2) | −1350(1) | 6758(1) | 52(1) | 1 |
| C32 | −164(2) | 202(2) | 6248(1) | 28(1) | 1 |
| C42 | −191(2) | 835(2) | 5872(1) | 25(1) | 1 |
| C52 | 1637(2) | 765(1) | 5697(1) | 21(1) | 1 |
| C512 | 2207(2) | −580(2) | 5684(1) | 25(1) | 1 |
| C62 | 1551(2) | 1371(2) | 5298(1) | 21(1) | 1 |
| C612 | 699(2) | 2633(2) | 5317(1) | 30(1) | 1 |
| C72 | 355(2) | 598(2) | 5028(1) | 25(1) | 1 |
| C82 | 433(2) | 948(2) | 4622(1) | 25(1) | 1 |
| C92 | 2369(2) | 852(2) | 4506(1) | 22(1) | 1 |
| C102 | 2510(2) | 804(2) | 4078(1) | 26(1) | 1 |
| C1012 | 1518(3) | −322(2) | 3922(1) | 37(1) | 1 |
| C1022 | 1733(2) | 1921(2) | 3869(1) | 32(1) | 1 |
| C112 | 4515(2) | 622(2) | 4018(1) | 26(1) | 1 |
| O1112 | 4748(2) | 713(2) | 3623(1) | 32(1) | 1 |
| O1122 | 6863(2) | −741(2) | 3667(1) | 61(1) | 1 |
| C1122 | 6029(3) | 23(2) | 3487(1) | 40(1) | 1 |
| C1132 | 6317(4) | 362(3) | 3096(1) | 61(1) | 1 |
| C122 | 5755(2) | 1531(2) | 4215(1) | 27(1) | 1 |
| C132 | 5569(2) | 1502(2) | 4633(1) | 25(1) | 1 |
| C142 | 3624(2) | 1758(1) | 4735(1) | 22(1) | 1 |
| C1412 | 3214(2) | 3107(2) | 4650(1) | 28(1) | 1 |
| C152 | 3491(2) | 1423(2) | 5155(1) | 21(1) | 1 |
| C162 | 4753(2) | 2152(2) | 5427(1) | 28(1) | 1 |
| C172 | 4871(2) | 1579(2) | 5812(1) | 30(1) | 1 |
| C182 | 3011(2) | 1465(2) | 5962(1) | 25(1) | 1 |
| O(1S) | 3045(2) | −1552(2) | 7659(1) | 49(1) | 1 |
| C(1S) | 3003(4) | −1056(2) | 8022(1) | 53(1) | 1 |

TABLE 2-continued

Atomic coordinates (×10⁴), equivalent isotropic displacement parameters ($Å^2 \times 10^3$) and site occupancies. U(eq) is defined as one third of the trace of the orthogonalized $U_{ij}$ tensor.

| Atom | x | y | z | U(eq) | Occ |
|---|---|---|---|---|---|
| O(2S) | 11395(3) | 6318(2) | −2383(1) | 65(1) | 1 |
| C(2S) | 9812(4) | 6433(3) | −2616(1) | 75(1) | 1 |
| O(3S) | 6530(3) | −1480(2) | −2551(1) | 81(1) | 1 |
| C(3S) | 6678(4) | −1336(4) | −2937(1) | 85(1) | 1 |

TABLE 3

Bond lengths and angles

| Bond | Length (Å) | Bonds | Angle (Degrees) |
|---|---|---|---|
| O11-C11 | 1.209(2) | O11-C11-C181 | 121.88(17) |
| C11-C181 | 1.511(2) | O11-C11-C21 | 119.88(17) |
| C11-C21 | 1.547(2) | C181-C11-C21 | 118.17(16) |
| C211-O221 | 1.447(2) | O221-C211-C21 | 107.30(17) |
| C211-C21 | 1.521(3) | C231-O221-C211 | 116.63(18) |
| O221-C231 | 1.340(3) | O231-C231-O221 | 122.33(19) |
| O231-C231 | 1.211(3) | O231-C231-C241 | 126.7(2) |
| C231-C241 | 1.493(3) | O221-C231-C241 | 110.9(2) |
| C21-C25'1 | 1.528(8) | C211-C21-C25'1 | 95.6(5) |
| C21-C31 | 1.543(3) | C211-C21-C31 | 111.31(17) |
| C21-C251 | 1.590(6) | C25'1-C21-C31 | 123.4(4) |
| C251-O271 | 1.199(2) | C211-C21-C11 | 106.35(16) |
| C251-O261 | 1.309(6) | C25'1-C21-C11 | 106.4(3) |
| C25'1-O27'1 | 1.217(9) | C31-C21-C11 | 111.72(15) |
| C25'1-O26'1 | 1.312(8) | C211-C21-C251 | 119.3(3) |
| C31-C41 | 1.525(2) | C25'1-C21-C251 | 25.4(3) |
| C41-C51 | 1.542(2) | C31-C21-C251 | 102.9(3) |
| C51-C511 | 1.547(2) | C11-C21-C251 | 105.14(19) |
| C51-C181 | 1.561(2) | O271-C251-O261 | 125.0(5) |
| C51-C61 | 1.587(2) | O271-C251-C21 | 124.3(4) |
| C61-C71 | 1.536(2) | O261-C251-C21 | 110.7(5) |
| C61-C611 | 1.540(2) | O27'1-C25'1-O26'1 | 126.1(7) |
| C61-C151 | 1.570(2) | O27'1-C25'1-C21 | 126.5(7) |
| C71-C81 | 1.527(2) | O26'1-C25'1-C21 | 107.4(6) |
| C81-C91 | 1.530(2) | C41-C31-C21 | 113.20(14) |
| C91-C141 | 1.557(2) | C31-C41-C51 | 112.95(14) |
| C91-C101 | 1.562(2) | C41-C51-C511 | 108.12(13) |
| C101-C1021 | 1.533(2) | C41-C51-C181 | 106.23(13) |
| C101-C1011 | 1.535(3) | C511-C51-C181 | 109.14(14) |
| C101-C111 | 1.539(2) | C41-C51-C61 | 112.03(13) |
| C111-O1111 | 1.4533(19) | C511-C51-C61 | 111.97(13) |
| C111-C121 | 1.511(2) | C181-C51-C61 | 109.17(13) |
| O1111-C1121 | 1.336(2) | C71-C61-C611 | 108.15(14) |
| O1121-C1121 | 1.207(3) | C71-C61-C151 | 108.56(12) |
| C1121-C1131 | 1.498(3) | C611-C61-C151 | 111.67(13) |
| C121-C131 | 1.533(2) | C71-C61-C51 | 109.32(13) |
| C131-C141 | 1.547(2) | C611-C61-C51 | 109.50(13) |
| C141-C1411 | 1.547(2) | C151-C61-C51 | 109.59(12) |
| C141-C151 | 1.567(2) | C81-C71-C61 | 113.96(13) |
| C151-C161 | 1.537(2) | C71-C81-C91 | 110.15(13) |
| C161-C171 | 1.523(3) | C81-C91-C141 | 110.46(13) |
| C171-C181 | 1.527(2) | C81-C91-C101 | 113.82(13) |
| O12-C12 | 1.210(2) | C141-C91-C101 | 117.76(13) |
| C12-C182 | 1.512(3) | C1021-C101-C1011 | 107.62(15) |
| C12-C22 | 1.547(2) | C1021-C101-C111 | 112.15(14) |
| C22-C212 | 1.535(3) | C1011-C101-C111 | 106.79(14) |
| C22-C252 | 1.543(3) | C1021-C101-C91 | 114.36(14) |
| C22-C32 | 1.544(3) | C1011-C101-C91 | 109.21(13) |
| C212-O222 | 1.437(2) | C111-C101-C91 | 106.44(13) |
| O222-C232 | 1.330(3) | O1111-C111-C121 | 107.67(13) |
| O232-C232 | 1.195(3) | O1111-C111-C101 | 108.65(13) |
| C232-C242 | 1.488(4) | C121-C111-C101 | 114.37(14) |
| C252-O272 | 1.196(3) | C1121-O1111-C111 | 117.37(14) |
| C252-O262 | 1.315(3) | O1121-C1121-O1111 | 123.44(18) |
| C32-C42 | 1.527(2) | O1121-C1121-C1131 | 124.91(18) |
| C42-C52 | 1.544(2) | O1111-C1121-C1131 | 111.60(18) |
| C52-C512 | 1.546(2) | C111-C121-C131 | 110.94(14) |
| C52-C182 | 1.559(2) | C121-C131-C141 | 112.89(14) |
| C52-C62 | 1.587(2) | C1411-C141-C131 | 107.22(13) |
| C62-C612 | 1.535(2) | C1411-C141-C91 | 113.99(14) |
| C62-C72 | 1.536(2) | C131-C141-C91 | 107.26(13) |
| C72-C82 | 1.523(2) | C1411-C141-C151 | 113.05(13) |
| C82-C92 | 1.532(2) | C131-C141-C151 | 108.16(13) |
| C92-C102 | 1.561(2) | C91-C141-C151 | 106.89(12) |
| C92-C142 | 1.567(2) | C161-C151-C141 | 114.80(13) |
| C102-C1012 | 1.535(3) | C161-C151-C61 | 110.02(13) |
| C102-C112 | 1.537(2) | C141-C151-C61 | 116.89(13) |
| C102-C1022 | 1.540(2) | C171-C161-C151 | 111.17(14) |
| C112-O1112 | 1.452(2) | C161-C171-C181 | 110.97(15) |
| C112-C122 | 1.509(2) | C11-C181-C171 | 111.57(15) |
| O1112-C1122 | 1.341(2) | C11-C181-C51 | 110.09(14) |
| O1122-C1122 | 1.210(3) | C171-C181-C51 | 113.34(13) |
| C1122-C1132 | 1.494(3) | O12-C12-C182 | 121.90(16) |
| C122-C132 | 1.529(2) | O12-C12-C22 | 120.15(17) |
| C132-C142 | 1.546(2) | C182-C12-C22 | 117.94(16) |
| C142-C1412 | 1.547(2) | C212-C22-C252 | 113.04(16) |
| C142-C152 | 1.572(2) | C212-C22-C32 | 111.88(16) |
| C152-C162 | 1.539(2) | C252-C22-C32 | 108.22(15) |
| C162-C172 | 1.527(2) | C212-C22-C12 | 105.53(15) |
| C172-C182 | 1.527(2) | C252-C22-C12 | 106.52(15) |
| O(1S)-C(1S) | 1.425(3) | C32-C22-C12 | 111.55(14) |
| O(2S)-C(2S) | 1.407(4) | O222-C212-C22 | 107.34(15) |
| O(3S)-C(3S) | 1.417(4) | C232-O222-C212 | 116.50(17) |
| | | O232-C232-O222 | 121.8(2) |
| | | O232-C232-C242 | 126.4(2) |
| | | O222-C232-C242 | 111.8(2) |
| | | O272-C252-O262 | 123.8(2) |
| | | O272-C252-C22 | 122.67(19) |
| | | O262-C252-C22 | 113.50(18) |
| | | C42-C32-C22 | 112.98(14) |
| | | C32-C42-C52 | 112.72(14) |
| | | C42-C52-C512 | 108.17(13) |
| | | C42-C52-C182 | 106.38(13) |
| | | C512-C52-C182 | 108.96(14) |
| | | C42-C52-C62 | 111.83(13) |
| | | C512-C52-C62 | 111.91(13) |
| | | C182-C52-C62 | 109.41(13) |
| | | C612-C62-C72 | 108.09(14) |
| | | C612-C62-C152 | 111.98(13) |
| | | C72-C62-C152 | 108.40(13) |
| | | C612-C62-C52 | 109.49(13) |
| | | C72-C62-C52 | 109.19(13) |
| | | C152-C62-C52 | 109.62(12) |
| | | C82-C72-C62 | 114.41(13) |
| | | C72-C82-C92 | 110.23(13) |
| | | C82-C92-C102 | 113.82(13) |
| | | C82-C92-C142 | 110.41(13) |
| | | C102-C92-C142 | 117.87(13) |
| | | C1012-C102-C112 | 106.78(15) |
| | | C1012-C102-C1022 | 108.25(15) |
| | | C112-C102-C1022 | 111.77(14) |
| | | C1012-C102-C92 | 109.24(14) |
| | | C112-C102-C92 | 106.21(13) |
| | | C1022-C102-C92 | 114.32(14) |
| | | O1112-C112-C122 | 107.86(13) |
| | | O1112-C112-C102 | 108.32(14) |
| | | C122-C112-C102 | 114.44(14) |
| | | C1122-O1112-C112 | 117.25(15) |
| | | O1122-C1122-O1112 | 123.40(18) |
| | | O1122-C1122-C1132 | 125.5(2) |
| | | O1112-C1122-C1132 | 111.02(19) |
| | | C112-C122-C132 | 111.08(14) |
| | | C122-C132-C142 | 112.59(14) |
| | | C132-C142-C1412 | 107.66(13) |
| | | C132-C142-C92 | 106.91(13) |
| | | C1412-C142-C92 | 114.07(14) |

TABLE 3-continued

Bond lengths and angles

| Bond | Length (Å) | Bonds | Angle (Degrees) |
|---|---|---|---|
| | | C132-C142-C152 | 108.14(13) |
| | | C1412-C142-C152 | 113.20(13) |
| | | C92-C142-C152 | 106.55(12) |
| | | C162-C152-C62 | 110.03(13) |
| | | C162-C152-C142 | 114.66(13) |
| | | C62-C152-C142 | 116.68(13) |
| | | C172-C162-C152 | 111.09(14) |
| | | C182-C172-C162 | 111.24(14) |
| | | C12-C182-C172 | 111.70(14) |
| | | C12-C182-C52 | 110.00(14) |
| | | C172-C182-C52 | 113.29(13) |

TABLE 4

Anisotropic displacement parameters (Å$^2$ × 10$^3$). The anisotropic displacement factor exponent takes the form: $-2\pi^2$ [h$^2$ a*$^2$ U11 + ... + 2 h k a*b*U12]

| Atom | U11 | U22 | U33 | U23 | U13 | U12 |
|---|---|---|---|---|---|---|
| O11 | 28(1) | 78(1) | 38(1) | −10(1) | −3(1) | 3(1) |
| C11 | 29(1) | 40(1) | 30(1) | 3(1) | 2(1) | 2(1) |
| C211 | 40(1) | 64(1) | 37(1) | 19(1) | 18(1) | 17(1) |
| O221 | 49(1) | 50(1) | 46(1) | 16(1) | 25(1) | 11(1) |
| O231 | 81(1) | 50(1) | 46(1) | 5(1) | 23(1) | 2(1) |
| C231 | 51(1) | 53(1) | 24(1) | 7(1) | 8(1) | 0(1) |
| C241 | 48(1) | 73(2) | 40(1) | 10(1) | 14(1) | −1(1) |
| C21 | 31(1) | 44(1) | 29(1) | −4(1) | 6(1) | 0(1) |
| C251 | 30(2) | 43(4) | 34(3) | 3(3) | 2(2) | 0(2) |
| O261 | 71(2) | 53(4) | 33(2) | −8(2) | −1(1) | −1(2) |
| O271 | 71(2) | 38(2) | 53(2) | −3(2) | −9(2) | −7(2) |
| C25'1 | 35(4) | 32(5) | 20(5) | 6(3) | 1(3) | 1(3) |
| O26'1 | 50(3) | 27(5) | 39(5) | 3(4) | −7(3) | −3(3) |
| O27'1 | 104(5) | 37(6) | 31(3) | −1(3) | −11(3) | 10(4) |
| C31 | 29(1) | 28(1) | 33(1) | 1(1) | 11(1) | 2(1) |
| C41 | 20(1) | 28(1) | 32(1) | 4(1) | 7(1) | 1(1) |
| C51 | 17(1) | 21(1) | 27(1) | 3(1) | 4(1) | 1(1) |
| C511 | 31(1) | 23(1) | 30(1) | −1(1) | 6(1) | −4(1) |
| C61 | 16(1) | 19(1) | 28(1) | 0(1) | 5(1) | −1(1) |
| C611 | 28(1) | 24(1) | 38(1) | −2(1) | 10(1) | −8(1) |
| C71 | 17(1) | 29(1) | 30(1) | 1(1) | 3(1) | 5(1) |
| C81 | 17(1) | 29(1) | 31(1) | 1(1) | 2(1) | 3(1) |
| C91 | 19(1) | 19(1) | 26(1) | −2(1) | 2(1) | 0(1) |
| C101 | 22(1) | 26(1) | 27(1) | −3(1) | 4(1) | 1(1) |
| C1011 | 39(1) | 39(1) | 28(1) | 5(1) | 4(1) | 12(1) |
| C1021 | 25(1) | 39(1) | 33(1) | −10(1) | 3(1) | −5(1) |
| C111 | 26(1) | 25(1) | 26(1) | −3(1) | 7(1) | −3(1) |
| O1111 | 32(1) | 32(1) | 27(1) | −2(1) | 8(1) | −5(1) |
| O1121 | 78(1) | 58(1) | 58(1) | −19(1) | 35(1) | −38(1) |
| C1121 | 42(1) | 33(1) | 39(1) | −3(1) | 17(1) | −6(1) |
| C1131 | 66(2) | 67(2) | 41(1) | −5(1) | 26(1) | −17(1) |
| C121 | 18(1) | 31(1) | 34(1) | −1(1) | 7(1) | 0(1) |
| C131 | 18(1) | 29(1) | 32(1) | 0(1) | 5(1) | 2(1) |
| C141 | 16(1) | 18(1) | 30(1) | 1(1) | 4(1) | 2(1) |
| C1411 | 28(1) | 20(1) | 38(1) | −3(1) | 8(1) | 2(1) |
| C151 | 16(1) | 18(1) | 29(1) | 1(1) | 3(1) | 0(1) |
| C161 | 23(1) | 34(1) | 33(1) | 5(1) | 5(1) | 9(1) |
| C171 | 19(1) | 43(1) | 31(1) | 4(1) | 2(1) | 6(1) |
| C181 | 20(1) | 31(1) | 27(1) | 4(1) | 4(1) | 3(1) |
| O12 | 27(1) | 88(1) | 39(1) | 15(1) | −3(1) | −5(1) |
| C12 | 26(1) | 37(1) | 32(1) | −5(1) | 2(1) | −7(1) |
| C22 | 30(1) | 31(1) | 30(1) | −2(1) | 6(1) | −4(1) |
| C212 | 37(1) | 36(1) | 36(1) | −7(1) | 12(1) | −5(1) |
| O222 | 44(1) | 46(1) | 53(1) | −18(1) | 21(1) | −5(1) |
| O232 | 88(2) | 70(1) | 117(2) | −52(1) | 31(1) | −6(1) |
| C232 | 58(1) | 46(1) | 33(1) | −7(1) | 5(1) | 10(1) |
| C242 | 59(2) | 95(2) | 65(2) | −16(2) | 22(1) | 23(2) |
| C252 | 30(1) | 46(1) | 35(1) | 1(1) | 6(1) | −4(1) |
| O262 | 72(1) | 50(1) | 34(1) | 3(1) | 3(1) | −3(1) |
| O272 | 68(1) | 34(1) | 51(1) | 4(1) | −2(1) | 3(1) |
| C32 | 25(1) | 28(1) | 34(1) | −1(1) | 8(1) | −4(1) |
| C42 | 18(1) | 25(1) | 34(1) | −3(1) | 6(1) | −1(1) |

TABLE 4-continued

Anisotropic displacement parameters (Å$^2$ × 10$^3$). The anisotropic displacement factor exponent takes the form: $-2\pi^2$ [h$^2$ a*$^2$ U11 + ... + 2 h k a*b*U12]

| Atom | U11 | U22 | U33 | U23 | U13 | U12 |
|---|---|---|---|---|---|---|
| C52 | 16(1) | 18(1) | 29(1) | −2(1) | 3(1) | −1(1) |
| C512 | 25(1) | 19(1) | 32(1) | 2(1) | 4(1) | 2(1) |
| C62 | 15(1) | 19(1) | 30(1) | 2(1) | 4(1) | 2(1) |
| C612 | 28(1) | 22(1) | 41(1) | 5(1) | 10(1) | 8(1) |
| C72 | 17(1) | 27(1) | 33(1) | 2(1) | 2(1) | −3(1) |
| C82 | 15(1) | 28(1) | 32(1) | 2(1) | 0(1) | −2(1) |
| C92 | 17(1) | 22(1) | 28(1) | 2(1) | 0(1) | 0(1) |
| C102 | 22(1) | 26(1) | 30(1) | 2(1) | 3(1) | −2(1) |
| C1012 | 40(1) | 40(1) | 31(1) | −4(1) | 3(1) | −12(1) |
| C1022 | 26(1) | 38(1) | 33(1) | 8(1) | 0(1) | 4(1) |
| C112 | 28(1) | 24(1) | 27(1) | 3(1) | 5(1) | 1(1) |
| O1112 | 33(1) | 33(1) | 31(1) | 2(1) | 7(1) | 3(1) |
| O1122 | 71(1) | 50(1) | 68(1) | 13(1) | 35(1) | 28(1) |
| C1122 | 43(1) | 34(1) | 44(1) | −3(1) | 19(1) | −1(1) |
| C1132 | 80(2) | 60(2) | 49(1) | −3(1) | 33(1) | 7(1) |
| C122 | 17(1) | 31(1) | 35(1) | 3(1) | 5(1) | 1(1) |
| C132 | 16(1) | 29(1) | 31(1) | 2(1) | 4(1) | −2(1) |
| C142 | 16(1) | 19(1) | 31(1) | 1(1) | 4(1) | −1(1) |
| C1412 | 25(1) | 20(1) | 38(1) | 2(1) | 6(1) | −1(1) |
| C152 | 16(1) | 17(1) | 29(1) | −1(1) | 2(1) | −1(1) |
| C162 | 21(1) | 32(1) | 33(1) | −4(1) | 2(1) | −10(1) |
| C172 | 19(1) | 37(1) | 33(1) | −4(1) | 1(1) | −7(1) |
| C182 | 20(1) | 27(1) | 29(1) | −3(1) | 3(1) | −4(1) |
| O(1S) | 60(1) | 44(1) | 42(1) | 7(1) | 7(1) | −9(1) |
| C(1S) | 67(2) | 55(1) | 39(1) | 2(1) | 10(1) | −2(1) |
| O(2S) | 73(1) | 48(1) | 77(1) | 11(1) | 11(1) | −6(1) |
| C(2S) | 56(2) | 53(2) | 116(2) | 23(2) | 14(2) | 4(2) |
| O(3S) | 54(1) | 96(2) | 96(1) | −54(1) | 18(1) | −10(1) |
| C(3S) | 68(2) | 87(2) | 103(3) | 37(2) | 28(2) | 19(2) |

TABLE 5

Hydrogen coordinates (×10$^4$) and isotropic displacement parameters (Å$^2$ × 10$^3$)

| Atom | x | y | z | U(eq) |
|---|---|---|---|---|
| H21A1 | 7963 | 2690 | −1892 | 56 |
| H21B1 | 9183 | 3002 | −1520 | 56 |
| H24A1 | 13417 | 3550 | −2368 | 80 |
| H24B1 | 12720 | 2181 | −2403 | 80 |
| H24C1 | 13966 | 2595 | −2047 | 80 |
| H261 | 7408 | −171 | −2299 | 78 |
| H26'1 | 7667 | −945 | −2073 | 59 |
| H3A1 | 9790 | −184 | −1249 | 36 |
| H3B1 | 11132 | 811 | −1395 | 36 |
| H4A1 | 10388 | 2173 | −936 | 31 |
| H4B1 | 11009 | 925 | −742 | 31 |
| H51A1 | 7227 | −356 | −954 | 42 |
| H51B1 | 6722 | −186 | −534 | 42 |
| H51C1 | 8712 | −595 | −620 | 42 |
| H61A1 | 9226 | 3517 | −99 | 44 |
| H61B1 | 8591 | 3590 | −531 | 44 |
| H61C1 | 10516 | 3029 | −402 | 44 |
| H7A1 | 9253 | 208 | −84 | 30 |
| H7B1 | 10881 | 1128 | −129 | 30 |
| H8A1 | 10035 | 2258 | 388 | 31 |
| H8B1 | 10404 | 876 | 506 | 31 |
| H91 | 7255 | 502 | 389 | 25 |
| H10A1 | 9893 | 255 | 1041 | 53 |
| H10B1 | 8201 | −572 | 911 | 53 |
| H10C1 | 8343 | 9 | 1317 | 53 |
| H10D1 | 8486 | 2202 | 1381 | 48 |
| H10E1 | 7620 | 3073 | 1063 | 48 |
| H10F1 | 9596 | 2529 | 1032 | 48 |
| H111 | 5215 | 247 | 892 | 31 |
| H11A1 | 3205 | 119 | 2023 | 85 |
| H11B1 | 3301 | 1531 | 1927 | 85 |
| H11C1 | 5104 | 804 | 2050 | 85 |
| H12A1 | 4616 | 2808 | 886 | 33 |

TABLE 5-continued

Hydrogen coordinates (×10$^4$) and isotropic displacement parameters (Å$^2$ × 10$^3$)

| Atom | x | y | z | U(eq) |
| --- | --- | --- | --- | --- |
| H12B1 | 3069 | 1799 | 844 | 33 |
| H13A1 | 3652 | 2594 | 252 | 31 |
| H13B1 | 4075 | 1174 | 269 | 31 |
| H14A1 | 6244 | 3808 | 568 | 43 |
| H14B1 | 6366 | 4072 | 135 | 43 |
| H14C1 | 8130 | 3680 | 385 | 43 |
| H151 | 6020 | 1060 | −186 | 25 |
| H16A1 | 4009 | 2692 | −326 | 36 |
| H16B1 | 5675 | 3485 | −445 | 36 |
| H17A1 | 4225 | 2594 | −978 | 37 |
| H17B1 | 4466 | 1274 | −798 | 37 |
| H181 | 7343 | 2804 | −999 | 31 |
| H21A2 | 1729 | 2155 | 6890 | 43 |
| H21B2 | 798 | 2545 | 6493 | 43 |
| H24A2 | −3763 | 3263 | 7255 | 108 |
| H24B2 | −3373 | 1851 | 7319 | 108 |
| H24C2 | −4117 | 2331 | 6920 | 108 |
| H262 | 2339 | −407 | 7311 | 77 |
| H3A2 | 18 | −677 | 6212 | 34 |
| H3B2 | −1348 | 313 | 6352 | 34 |
| H4A2 | −519 | 1695 | 5903 | 30 |
| H4B2 | −1129 | 458 | 5702 | 30 |
| H51A2 | 2645 | −844 | 5933 | 37 |
| H51B2 | 3166 | −674 | 5514 | 37 |
| H51C2 | 1169 | −1075 | 5597 | 37 |
| H61A2 | 730 | 3032 | 5076 | 45 |
| H61B2 | 1375 | 3118 | 5506 | 45 |
| H61C2 | −553 | 2554 | 5381 | 45 |
| H7A2 | 722 | −260 | 5058 | 30 |
| H7B2 | −907 | 663 | 5095 | 30 |
| H8A2 | −6 | 1788 | 4585 | 30 |
| H8B2 | −358 | 406 | 4466 | 30 |
| H92 | 2781 | 34 | 4595 | 27 |
| H10A2 | 217 | −209 | 3932 | 55 |
| H10B2 | 1902 | −1033 | 4069 | 55 |
| H10C2 | 1800 | −445 | 3664 | 55 |
| H10D2 | 1657 | 1761 | 3602 | 48 |
| H10E2 | 2519 | 2620 | 3923 | 48 |
| H10F2 | 527 | 2095 | 3948 | 48 |
| H112 | 4878 | −209 | 4103 | 32 |
| H11A2 | 7145 | −217 | 2993 | 92 |
| H11B2 | 6832 | 1177 | 3090 | 92 |
| H11C2 | 5162 | 347 | 2948 | 92 |
| H12A2 | 5464 | 2352 | 4119 | 33 |
| H12B2 | 7015 | 1347 | 4164 | 33 |
| H13A2 | 6386 | 2114 | 4753 | 30 |
| H13B2 | 5947 | 697 | 4730 | 30 |
| H14A2 | 3632 | 3602 | 4864 | 41 |
| H14B2 | 1914 | 3215 | 4600 | 41 |
| H14C2 | 3838 | 3357 | 4433 | 41 |
| H152 | 3945 | 572 | 5177 | 25 |
| H16A2 | 5970 | 2185 | 5333 | 34 |
| H16B2 | 4300 | 2992 | 5443 | 34 |
| H17A2 | 5424 | 766 | 5799 | 36 |
| H17B2 | 5652 | 2082 | 5983 | 36 |
| H182 | 2533 | 2304 | 5988 | 30 |
| H(1S) | 2554 | −2237 | 7653 | 73 |
| H(1S1) | 3830 | −1509 | 8193 | 80 |
| H(1S2) | 1779 | −1113 | 8103 | 80 |
| H(1S3) | 3372 | −205 | 8019 | 80 |
| H(2S) | 11242 | 5791 | −2220 | 98 |
| H(2S1) | 8881 | 6832 | −2481 | 112 |
| H(2S2) | 9391 | 5628 | −2696 | 112 |
| H(2S3) | 10061 | 6919 | −2833 | 112 |
| H(3S) | 5455 | −1499 | −2486 | 121 |
| H(3S1) | 5781 | −748 | −3035 | 127 |
| H(3S2) | 6468 | −2116 | −3061 | 127 |
| H(3S3) | 7887 | −1044 | −2981 | 127 |

TABLE 6

Hydrogen bonds with H . . . A < r(A) + 2.000 Å and DHA > 110 °

| D-H | d(D-H) | d(H . . . A) | DHA | d(D . . . A) | A |
| --- | --- | --- | --- | --- | --- |
| O26-H26__1a | 0.84 | 1.807 | 169.46 | 2.638 | O3S |
| O26'-H26'__1b | 0.84 | 1.961 | 166.92 | 2.786 | O3S |
| O26-H26__2 | 0.84 | 1.836 | 175.85 | 2.674 | O1S |
| O1S-H1S | 0.84 | 1.815 | 176.48 | 2.654 | O2S [x − 1, y − 1, z + 1] |

TABLE 6-continued

| Hydrogen bonds with H . . . A < r(A) + 2.000 Å and DHA > 110 ° | | | | | |
|---|---|---|---|---|---|
| D-H | d(D-H) | d(H . . . A) | DHA | d(D . . . A) | A |
| O2S-H2S | 0.84 | 1.986 | 160.28 | 2.791 | O23_1 |
| O3S-H3S | 0.85 | 1.905 | 179.68 | 2.755 | O1S [x, y, z − 1] |

The invention claimed is:

1. 3β,28-diacetoxy-18-oxo-19,20,21,29,30-pentanorlupan-22-oic acid methanol solvate or pharmaceutically acceptable salt or ester thereof.

2. 3β,28-diacetoxy-18-oxo-19,20,21,29,30-pentanorlupan-22-oic acid•1.5MeOH or pharmaceutically acceptable salt or ester thereof.

3. The compound of claim 1 or claim 2 having at least X-ray diffraction peaks at 14.7 and 16.0.

4. The compound of claim 3 having a powder X-ray diffraction pattern with peaks at 14.7, 16.0, 16.7, 18.8, 8.3, 20.4, and 22.7.

5. The compound of claim 1 or claim 2 having unit cell dimensions a=(7).4459(9) Å, α=90°, b =11.0454(9) Å, β=94.002(11)°, c=36.178(4) Å, γ=90°.

6. The compound of claim 1 or claim 2 having a monoclinic crystalline form.

7. 3β,28-diacetoxy-18-oxo-19,20,21,29,30-pentanorlupan-22-oic acid acetonitrile solvate.

8. 3β,28-diacetoxy-18-oxo-19,20,21,29,30-pentanorlupan-22-oic acid acetone solvate.

9. A method of treating a proliferative disorder in a mammal, comprising administering an effective amount of a compound of any one of claims 1, 2, 7 or 8 to said mammal, such that said mammal is treated.

10. A pharmaceutical composition comprising a compound according to any one of claims 1, 2, 7 or 8 admixed with a pharmaceutically acceptable diliuent, excipient or carrier.

11. A process for preparing a compound according claim 1 or claim 2 which comprises crystallising 3β,28-diacetoxy-18-oxo-19,20,21,29,30-pentanorlupan-22-oic acid from a $CHCl_3$/EtOAc/MeOH solvent system.

12. A process for the preparation of 3β,28-diacetoxy-18-oxo-19,20,21,29,30-pentanorlupan-22-oic acid (7) which comprises reacting the anhydride of 3β,28-diacetoxy-21,22-secolup-18-ene-21,22-dioic acid (6) with ruthenium (III) chloride and $NaIO_4$ in a MeCN/EtOAc/$H_2O$ solvent system and optionally converting the resultant 3β,28-diacetoxy-18-oxo-19,20,21,29,30-pentanorlupan-22-oic acid to a compound of claim 1 or claim 2.

13. The method of claim 9, wherein said proliferative disorder is a cancer.

14. The method of claim 9, wherein said proliferative disorder is a leukemia.

15. The method of claim 9, wherein said subject is a human.

* * * * *